US010265501B2

(12) United States Patent
Farnan et al.

(10) Patent No.: US 10,265,501 B2
(45) Date of Patent: *Apr. 23, 2019

(54) MALLEABLE CANNULA

(71) Applicant: CircuLite, Inc., Teaneck, NJ (US)

(72) Inventors: Robert C. Farnan, Fort Lauderdale, FL (US); Arielle Drummond, Silver Spring, MD (US)

(73) Assignee: CircuLite, Inc., Teaneck, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/718,629

(22) Filed: Sep. 28, 2017

(65) Prior Publication Data

US 2018/0015253 A1   Jan. 18, 2018

Related U.S. Application Data

(63) Continuation of application No. 14/805,942, filed on Jul. 22, 2015, now Pat. No. 9,782,559.

(Continued)

(51) Int. Cl.
*A61M 25/00* (2006.01)
*A61M 1/10* (2006.01)
(Continued)

(52) U.S. Cl.
CPC ........ *A61M 25/0023* (2013.01); *A61M 1/101* (2013.01); *A61M 1/1008* (2014.02);
(Continued)

(58) Field of Classification Search
CPC .... A61M 1/1008; A61M 1/101; A61M 1/122; A61M 25/0023; A61M 25/0054; A61M 5/142
See application file for complete search history.

(56) References Cited

U.S. PATENT DOCUMENTS 4,976,688 A   12/1990   Rosenblum
5,269,752 A   12/1993   Bennett
(Continued)

FOREIGN PATENT DOCUMENTS

CA   1185862 A   4/1985
EP   1656963 A1   5/2006
(Continued)

OTHER PUBLICATIONS

European Patent Office, International Search Report and Written Opinion in PCT Application Serial No. PCT/US2015/041982, dated Oct. 29, 2015.

(Continued)

*Primary Examiner* — Brandy S Lee
(74) *Attorney, Agent, or Firm* — Christopher & Weisberg, P.A.

(57) ABSTRACT

A malleable cannula (50) for fluidically coupling with an anatomical structure includes a flexible cannula body wall (64) having a proximal end (68), a distal end (70), and a lumen (72) extending longitudinally between the proximal end (68) and the distal end (70). The proximal end (68) defines a first opening (80) to the lumen (72) and the distal end (70) defining a second opening (82) to the lumen (72). A channel is defined by a portion of the cannula body wall and extends longitudinally from the distal end (70) toward the proximal end (68). The channel has a first end oriented toward the proximal end of the cannula body wall. A malleable member (100) is provided within the channel and is fixedly connected to the cannula body wall (64) at the first end of the channel. The malleable member (100) is configured to assume and maintain a formed shape of the cannula body wall (64).

11 Claims, 6 Drawing Sheets

Related U.S. Application Data

(60) Provisional application No. 62/043,612, filed on Aug. 29, 2014.

(51) Int. Cl.
 *A61M 5/142* (2006.01)
 *A61M 1/12* (2006.01)

(52) U.S. Cl.
 CPC ........ *A61M 5/142* (2013.01); *A61M 25/0054* (2013.01); *A61M 1/122* (2014.02)

(56) References Cited

U.S. PATENT DOCUMENTS

| | | |
|---|---|---|
| 5,329,923 A | 7/1994 | Lundquist |
| 5,423,745 A | 6/1995 | Todd et al. |
| 6,022,343 A | 2/2000 | Johnson et al. |
| 6,544,215 B1 | 4/2003 | Bencini et al. |
| 6,976,979 B2 | 12/2005 | Lawrence et al. |
| 7,637,901 B2 | 12/2009 | Lawrence et al. |
| 9,782,559 B2 * | 10/2017 | Farnan ................. A61M 5/142 |
| 2003/0144657 A1 | 7/2003 | Bowe et al. |
| 2004/0087932 A1 | 5/2004 | Lawrence et al. |
| 2013/0304187 A1 | 11/2013 | Yamashita |

FOREIGN PATENT DOCUMENTS

| | | |
|---|---|---|
| WO | 2010135437 A2 | 11/2010 |
| WO | 2011035327 A1 | 3/2011 |
| WO | 2013063396 A1 | 5/2013 |

OTHER PUBLICATIONS

European Patent Office, 2nd Written Opinion in PCT Application Serial No. PCT/US2015/041982, dated Sep. 8, 2016.
European Patent Office, International Preliminary Report on Patentability in PCT Application Serial No. PCT/US2015/041982, dated Dec. 6, 2016.

* cited by examiner

MALLEABLE CANNULA

CROSS-REFERENCE TO RELATED APPLICATION

This application is a continuation of U.S. patent application Ser. No. 14/805,942, filed Jul. 22, 2015 (pending), which claims the priority of application Ser. No. 62/043,612 filed Aug. 29, 2014 (expired), the disclosures of which are hereby incorporated by reference herein.

TECHNICAL FIELD

The present invention relates generally to medical devices for assisting in the conduction of bodily fluids and, more particularly, to cannulae for use in moving bodily fluids.

BACKGROUND

During surgical procedures, various devices and methods have been utilized to assist in conducting bodily fluids. For example, in circulatory assistance, a blood pump may be fluidically attached to a patient's heart, and/or to surrounding vascular structure, by a cannula so that the blood pump may be located remotely and assist the heart in circulating blood. Cannulae may be used in surgical procedures involving other bodily organs as well.

It is often desirable to use a malleable cannula which may be bent into a particular configuration that is maintained during use. In this manner, a malleable cannula may be bent into a configuration that minimizes interference with surrounding structures, such as bodily organs. In known cannulae, such malleability is provided by a malleable member, such as a tube or rod, provided within and extending along a length of the cannula body. However, there remains a need for improvement in the manners in which malleable members are contained within and anchored to cannula bodies.

SUMMARY

An exemplary embodiment of a malleable cannula for fluidically coupling with an anatomical structure includes a flexible cannula body wall having a proximal end, a distal end, and a lumen extending longitudinally between the proximal end and the distal end. The proximal end defines a first opening to the lumen and the distal end defining a second opening to the lumen. A channel is defined by a portion of the cannula body wall and extends longitudinally from the distal end toward the proximal end. The channel has a first end oriented toward the proximal end of the cannula body wall. A malleable member is provided within the channel and is fixedly connected to the cannula body wall at the first end of the channel. The malleable member is configured to assume and maintain a formed shape of the cannula body wall.

An exemplary method of positioning a malleable cannula relative to an anatomical structure of a patient is also provided. The malleable cannula includes a flexible cannula body wall having a proximal end, a distal end, and a lumen that extends longitudinally between the proximal end and the distal end. The proximal end of the cannula body wall defines a first opening to the lumen and the distal end of the cannula body wall defines a second opening to the lumen. The malleable cannula further includes a cannula tip coupled to the distal end of the cannula body wall. The method includes inserting the cannula tip into an interior portion of the anatomical structure so that the lumen is in fluidic communication with the interior portion. The method further includes bending the cannula body wall along its longitudinal axis into a formed shape to accommodate an outer periphery of the anatomical structure or of an adjacent structure. Bending the cannula body wall includes bending a malleable member that substantially maintains the formed shape. The malleable member is arranged within a channel defined by a portion of the cannula body wall and extends longitudinally from the distal end of the cannula body wall toward the proximal end. The channel has a first end oriented toward the proximal end of the cannula body wall, and the malleable member is fixedly connected to the cannula body wall at the first end of the channel.

Various additional features and advantages of the invention will become more apparent to those of ordinary skill in the art upon review of the following detailed description of the illustrative embodiments taken in conjunction with the accompanying drawings.

DETAILED DESCRIPTION

Figure 1:
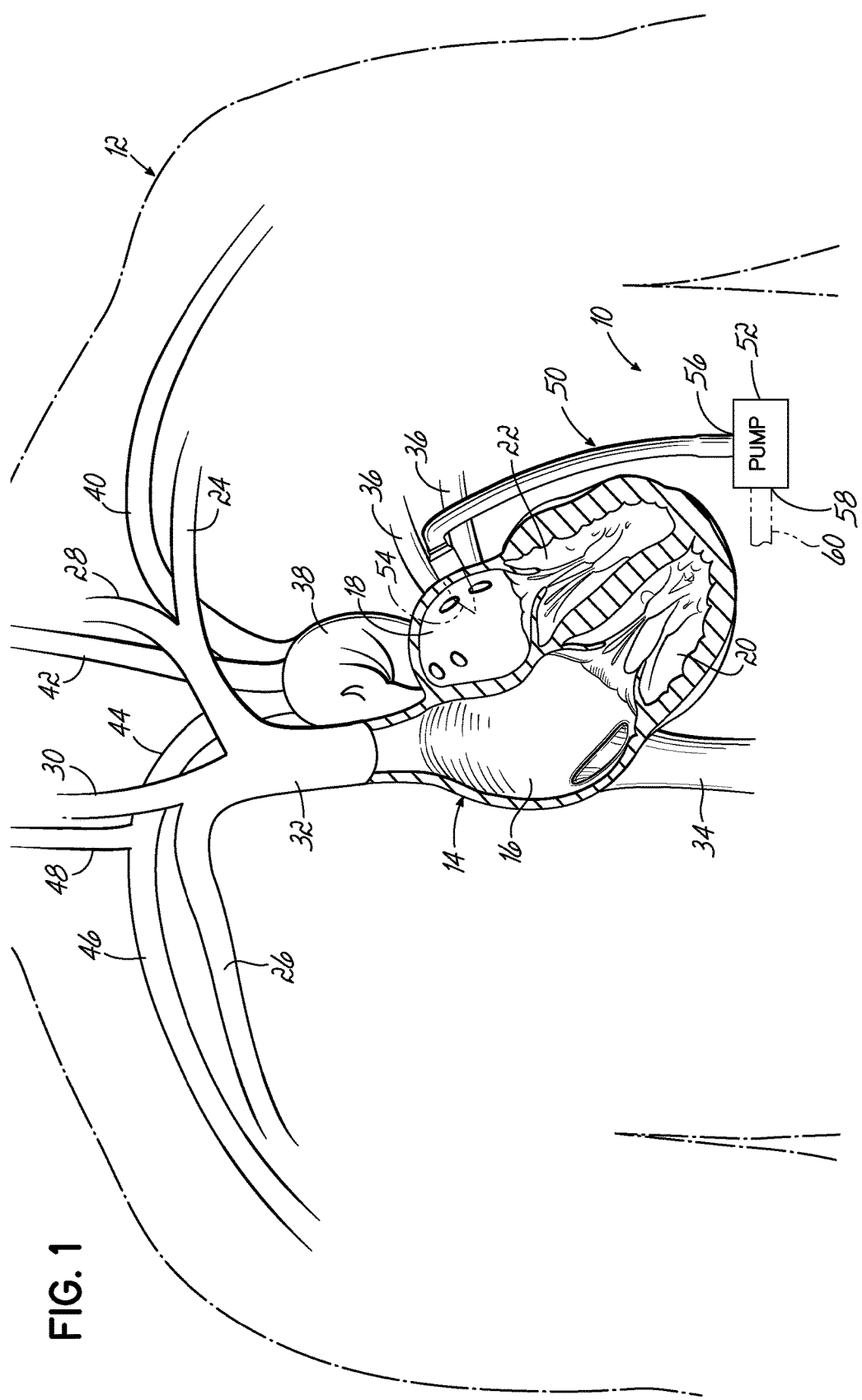
FIG. 1 is a schematic representation of chest anatomy of a human patient and shows a cardiac assist system including a malleable cannula according to an embodiment of the invention.

Referring to the figures, FIG. 1 shows a circulatory assist device 10 implanted in a patient 12. For illustrative purposes, certain anatomy is shown, including, the heart 14 of the patient 12 having a right atrium 16, a left atrium 18, a right ventricle 20, and a left ventricle 22. Blood from the left and right subclavian veins 24, 26 and the left and right jugular veins 28, 30 enters the right atrium 16 through the superior vena cava 32 while blood from the lower parts of the body enters the right atrium 16 through the inferior vena cava 34. The blood is pumped from the right atrium 16, to the right ventricle 20, and to the lungs (not shown) to be oxygenated. Blood returning from the lungs enters the left atrium 18 via the pulmonary veins 36 and is pumped into the left ventricle 22. Blood leaving the left ventricle 22 enters the aorta 38 and flows into the left subclavian artery 40, the left common carotid 42, and the brachiocephalic trunk 44, including the right subclavian artery 46 and the right common carotid 48.

With respect to the implanted circulatory assist device 10, a cannula 50 constructed according to one illustrative example of the invention, may extend between the heart 14 and a fluid pump 52. The fluid pump 52 may be any implantable or extracorporeal pump that is radially and/or axially driven. Persons skilled in this art will appreciate that other types of pumps may be used in other embodiments and may include pumps such as those described in U.S. Pat. No. 8,157,720, entitled HEART ASSIST SYSTEM, the disclosure of which is incorporated herein by reference in its entirety. Other pumps may include those that are commercially-available, such as the SYNERGY Pocket Micro-Pump from CircuLite Inc. (Saddle Brook, N.J.).

The cannula 50 is fitted with a distally-positioned tip 54, shown in phantom, that is configured to extend through a wall of the heart 14 into an interior chamber thereof. In one embodiment, as shown, the tip 54 may be inserted into the left atrium 18 adjacent to the pulmonary veins 36. The cannula 50 may extend from a first port 56 of the pump 52 to the left atrium 18 and may be secured with one or more sutures (not shown). A second cannula 60, shown partially in phantom, may extend from a second port 58 of the pump 52 to a vascular structure, such as the aorta 38, and may be secured thereto with one or more sutures (not shown), for example. In one embodiment, the first and second ports 56, 58 may be inflow and outflow ports, respectively, such that the cannula 50 operates as an inflow cannula and the second cannula 60 operates as an outflow cannula.

While the cannula 50 is shown for use with a circulatory assist device 10 coupled with the heart 14, persons skilled in the art will appreciate that the cannula 50 may be adapted for use in a variety of other medical applications as well, such as dialysis or colostomy, for example.

Figure 2:
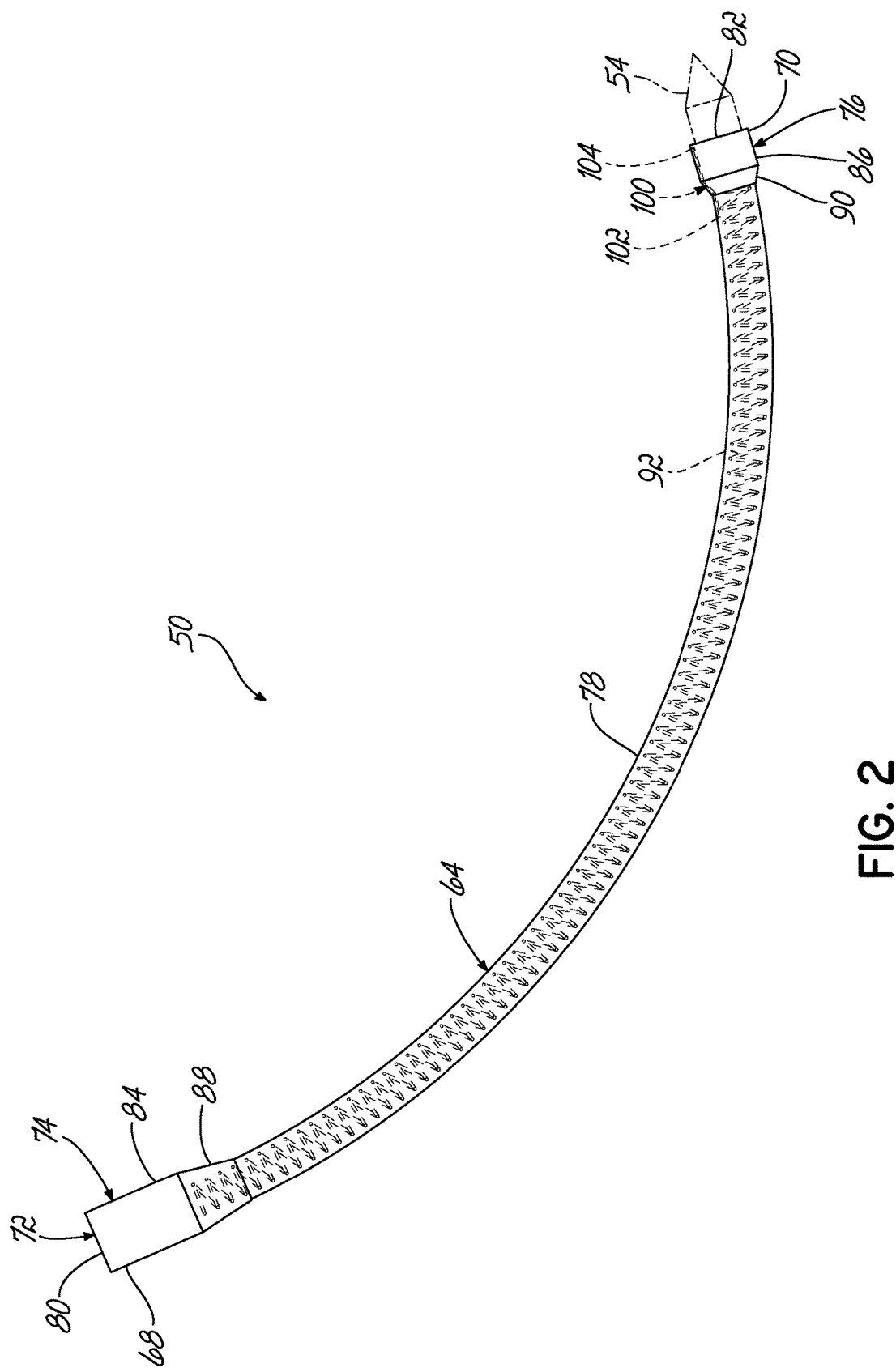
FIG. 2 is a front elevation view showing the cannula.

Referring to FIG. 2, additional features of the cannula 50 are shown. Persons skilled in the art will appreciate that the features of the cannula 50 described below may be applied to any number of additional cannulae used in combination with the cannula 50, for example the second cannula 60 of the circulatory assist device 10. The cannula 50 includes a flexible, elongate cannula body wall 64 having a proximal end 68 and a distal end 70, and defining a lumen 72 extending longitudinally between the proximal end 68 and the distal end 70. The body wall 64 includes a proximal hub 74 formed at the proximal end 68, a distal hub 76 formed at the distal end 70, and a tubular medial portion 78 extending between the proximal hub 74 and the distal hub 76. The proximal hub 74 defines a first opening 80 to the lumen 72 at the proximal end 68, and the distal hub 76 defines a second opening 82 to the lumen 72 at the distal end 70.

Figure 3:
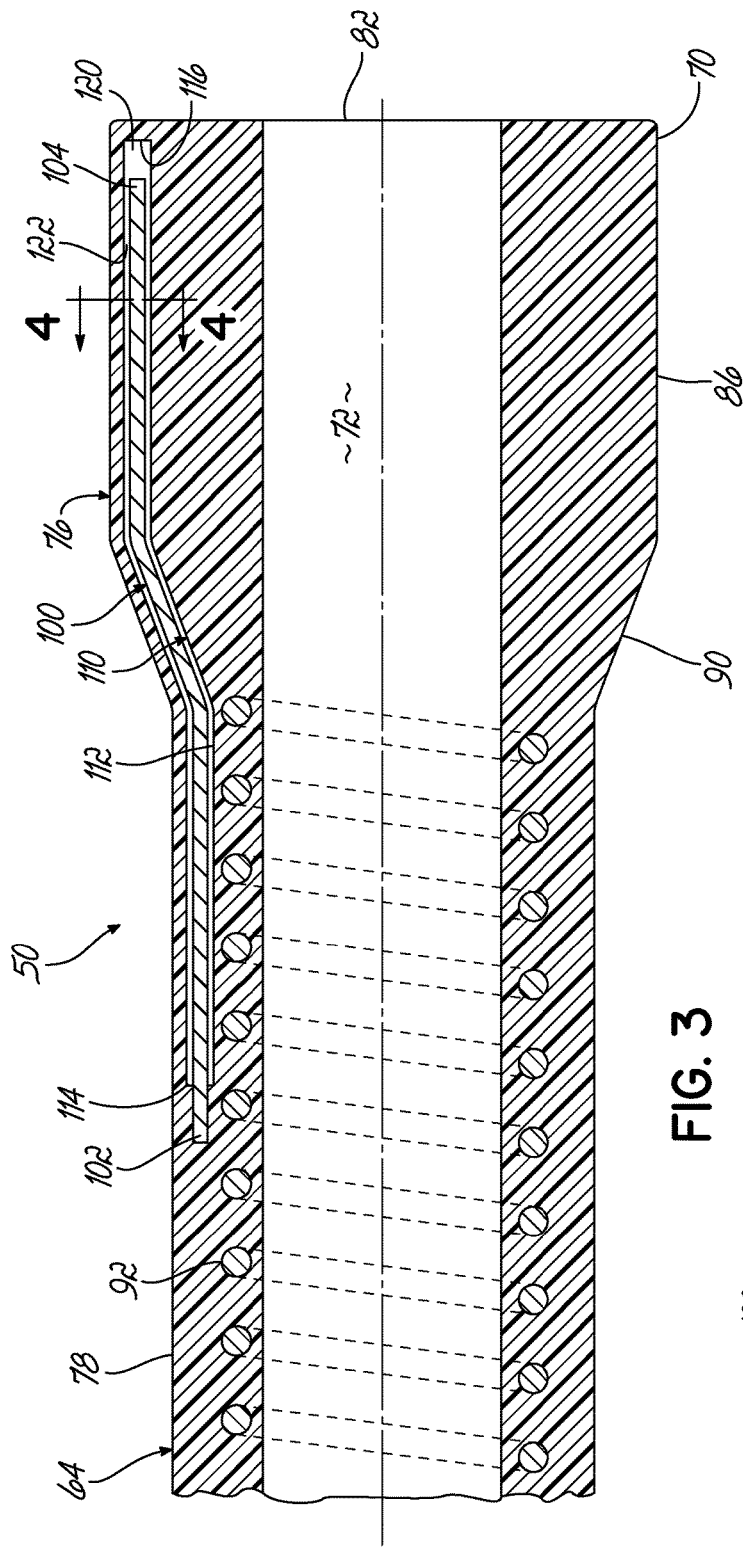
FIG. 3 is a longitudinal cross-sectional view of a distal portion of the malleable cannula shown in FIG. 2.

The proximal hub 74 and the distal hub 76 may each include a cylindrical portion 84, 86 and a tapered portion 88, 90, respectively. At each tapered portion 88, 90, an outer diameter defined the cylindrical portion 84, 86 tapers down to a smaller outer diameter defined by the medial portion 78 of the body wall 64. In this regard, as shown in FIGS. 3 and 6-7, the proximal hub 74 and distal hub 76 may each be formed with a radial wall thickness that is greater than a radial wall thickness of the medial portion 78. Additionally, the body wall 64 may be formed with cross-sectional shapes that are substantially circular, or with any other suitable cross-sectional shapes.

The cannula 50 may include a flexible reinforcement member 92, shown in the form of a coil, for substantially maintaining a cross-sectional shape of the lumen 72 during manipulation of the cannula 50, such as during bending of the cannula 50 along its longitudinal axis. Thereby, the reinforcement member 92 may substantially reduce the likelihood of kink formation in the cannula body wall 64. The reinforcement member 92 may be embedded within the body wall 64 to surround the lumen 72, and may extend a full length of the medial portion 78. In one embodiment, the reinforcement member 92 may extend proximally into the tapered portion 88 of the proximal hub 74, as shown.

A malleable member 100, represented in FIG. 2 by a dashed line, is arranged at the distal end 70 of the body wall 64. The malleable member 100 includes a proximal end 102 oriented toward the proximal end 68 of the body wall 64 and a distal end 104 oriented toward the distal end 70 of the body wall 64. In that regard, the malleable member 100 extends longitudinally from the distal end 70 of the body wall 64 toward the proximal end 68 thereof for any suitable length. For example, in the embodiment shown, the malleable member 100 extends proximally from the cylindrical portion 86 of the distal hub 76, through the tapered portion 90, and into a distal portion of the tubular medial portion 78 of the body wall 64, such that the proximal end 102 of the malleable member 100 overlies a distal portion of the flexible reinforcement member 92.

Figure 6A:
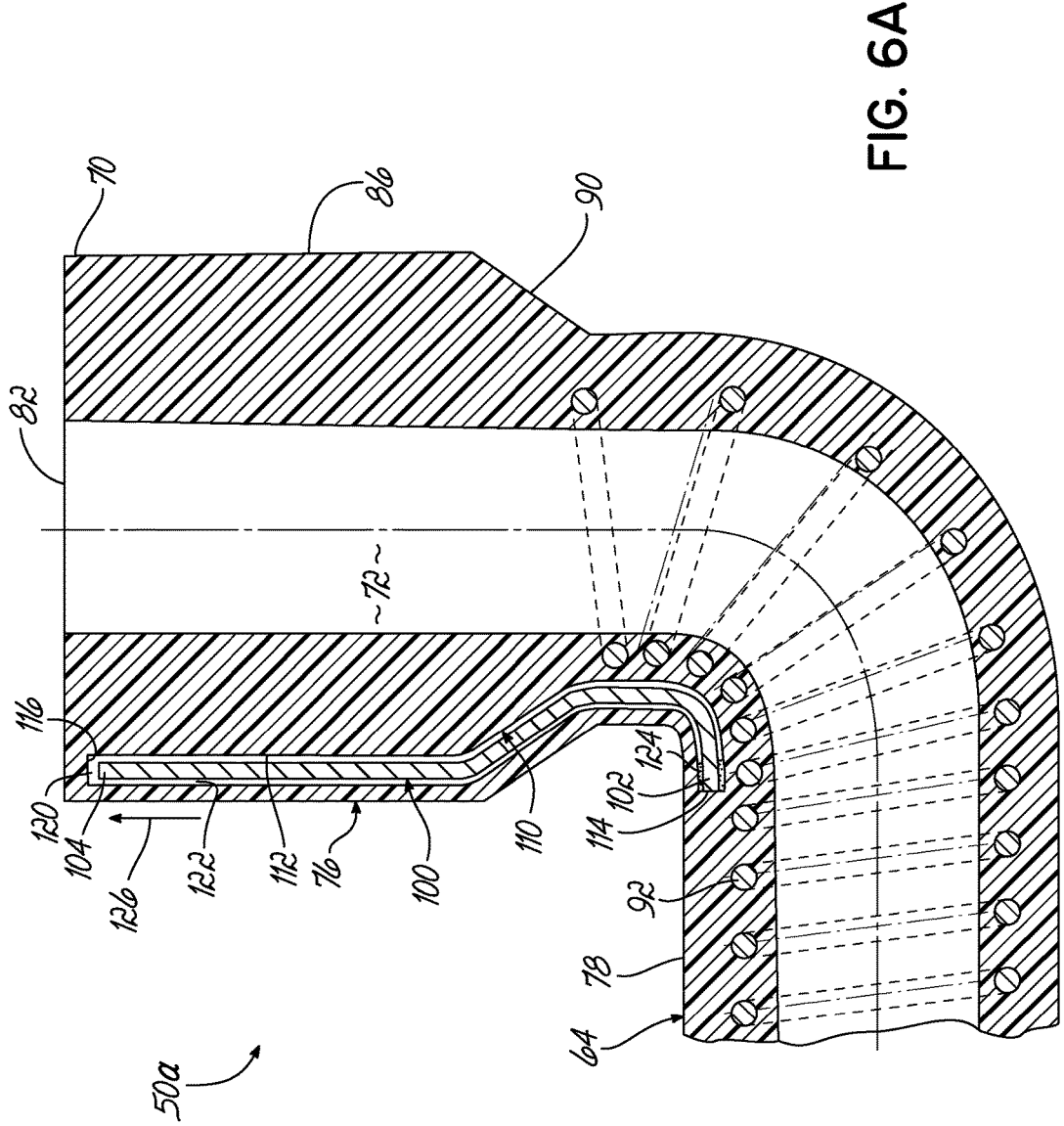
FIG. 6A is a cross-sectional view similar to FIG. 3, showing a distal portion of a malleable cannula of another embodiment in a first bent configuration.

The malleable member 100 is configured to assume and maintain a formed shape of the cannula 50 when the cannula 50 is bent along its longitudinal axis at a longitudinal location that includes the malleable member 100, for example as shown in FIGS. 6 and 6A. In this manner, the cannula 50 may be shaped by a user and substantially maintain its formed shape so as to avoid undesired contact with or to otherwise conform to adjacent structure, such as an anatomical structure, including bodily organs or vascular structures, for example. The malleable member 100 may be formed of any suitable malleable material, such as stainless steel, for example.

The distal hub 76 of the cannula 50 may be fitted with a cannula tip 54, represented in FIGS. 1 and 2 by phantom lines. The tip 54 may be constructed from a metallic material and, for example, may be of the type shown and described in U.S. application Ser. No. 13/788,039, entitled MALLEABLE CANNULA, the disclosure of which is incorporated herein by reference in its entirety. The tip 54 is configured to be inserted into an anatomical structure of a patient, such as an organ or a blood vessel, for arranging the cannula lumen 72 into fluidic communication with an interior portion of the anatomical structure so that a medical fluid, such as a bodily fluid, may be drawn from or delivered to the interior portion of the structure through the lumen 72.

Referring to FIG. 3, a distal portion of an exemplary embodiment of the malleable cannula 50 is shown. Similar reference numerals refer to similar features shown in FIG. 2. A channel 110 is provided within a distal portion of the body wall 64 near the distal end 70, and is adapted to house the malleable member 100 therein. The channel 110 is bounded in a radial direction by a channel wall 112 defined by the body wall 64. The channel wall 112 extends longitudinally and circumferentially surrounds the malleable member 100. The channel 110 includes a first end 114 oriented toward the proximal end 68 of the cannula body wall 64, and a second end 116 oriented toward the distal end 70 of the body wall 64. In the embodiment shown, the first end 114 is formed within the medial portion 78 of the body wall 64, and channel 110 extends distally through the tapered portion 90 and into the cylindrical portion 86 of the distal hub 76. In alternative embodiments, the channel 110 may extend through and open to the distal end 70 of the body wall 64.

Additionally, the channel 110 and the malleable member 100 contained therein may extend proximally to any suitable location along the length of the cannula body wall 64. In one embodiment, as shown, the channel 110 and the malleable member 100 may extend proximally to a location within a distal portion of the medial portion 78, for example to a location that is adjacent to the tapered portion 90 of the distal hub 76. In an alternative embodiment, though not shown, the channel 110 and the malleable member 100 may extend proximally for a full length of the medial portion 78 up to or into the proximal hub 74, for example. In this manner, the malleable cannula 50 may be formed with a malleable portion, defined by the portion of the cannula containing the malleable member 100, and with a non-malleable portion, defined by the portion of cannula 50 not containing the malleable member 100. Each of the malleable portion and the non-malleable portion may be flexible.

The channel 110 and the malleable member 100 contained therein may be positioned radially outward of the reinforcement member 92, and may generally conform to a radially outer surface of the body wall 64. For example, as shown in FIG. 3, the channel 110 substantially conforms to a radially outer surface collectively defined by the medial portion 78, the tapered portion 90, and the cylindrical portion 86 of the distal hub 76. In an alternative embodiment, though not shown, the channel 110 and the malleable member 100 may extend substantially parallel to the longitudinal axis of the cannula body wall 64 and the lumen 72.

The proximal end 102 of the malleable member 100 is fixedly connected to the cannula body wall 64 at the first end 114 of the channel 110. In one embodiment, as shown in FIG. 3, the proximal end 102 of the malleable member 100 is embedded within the body wall 64 at the first end 114 of the channel 110. The distal end 104 of the malleable member 100 extends freely toward the second end 116 of the channel 110 at the distal end 70 of the cannula body wall 64. In this regard, a longitudinal gap 120 may be provided between the distal end 104 of the malleable member 100 and the second end 116 of the channel 110. When the malleable cannula 50a is bent into a formed shape, as described in greater detail below, the distal end 104 of the malleable member 100 may slide longitudinally through the gap 120 so as to not contact the second end 116 of the channel 110. Furthermore, as shown, the channel 110 may be sized such that a circumferentially, longitudinally extending gap 122 is provided between the malleable member 100 and the channel wall 112. In alternative embodiments, the channel 110 may be sized such that the longitudinally extending channel wall 112 contacts the malleable member 100.

Figure 5:
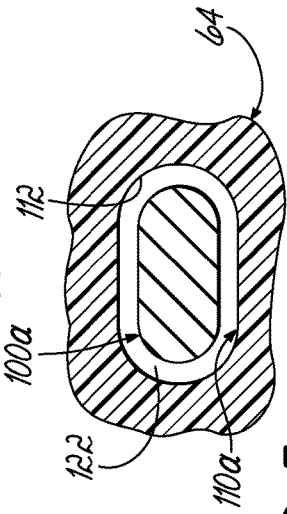
FIG. 5 is a view similar to FIG. 4, showing a malleable member and a channel of another embodiment.
Figure 4:
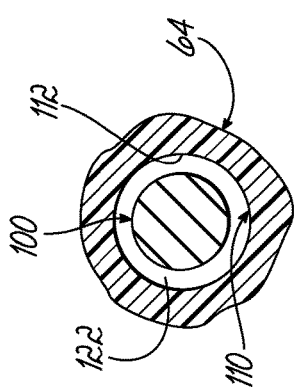
FIG. 4 is a cross-sectional view taken along section line 4-4 in FIG. 3, showing a malleable member and a channel according to an embodiment of the invention.

Referring to FIGS. 3-5, the malleable member 100 may be in the form of a malleable strip, such as a wire, with any suitable cross-sectional size and shape. In that regard, a cross-sectional size and shape of the channel 110 preferably accommodates the cross-sectional size and shape of the malleable member 100. In one embodiment, the malleable member 100 and the channel 110 may be formed with cross-sectional shapes that are substantially constant along the respective lengths of the malleable member 100 and the channel 110, such that the malleable member 100 may slide longitudinally relative to the channel wall 112 when the cannula 50a is bent along its longitudinal axis. FIG. 4 shows one embodiment in which the malleable member 100 and the channel 110 are formed with circular cross-sectional shapes. FIG. 5 shows another embodiment in which a malleable member 100a and a channel 110a are formed with flattened, rounded cross-sectional shapes.

Figure 6B:
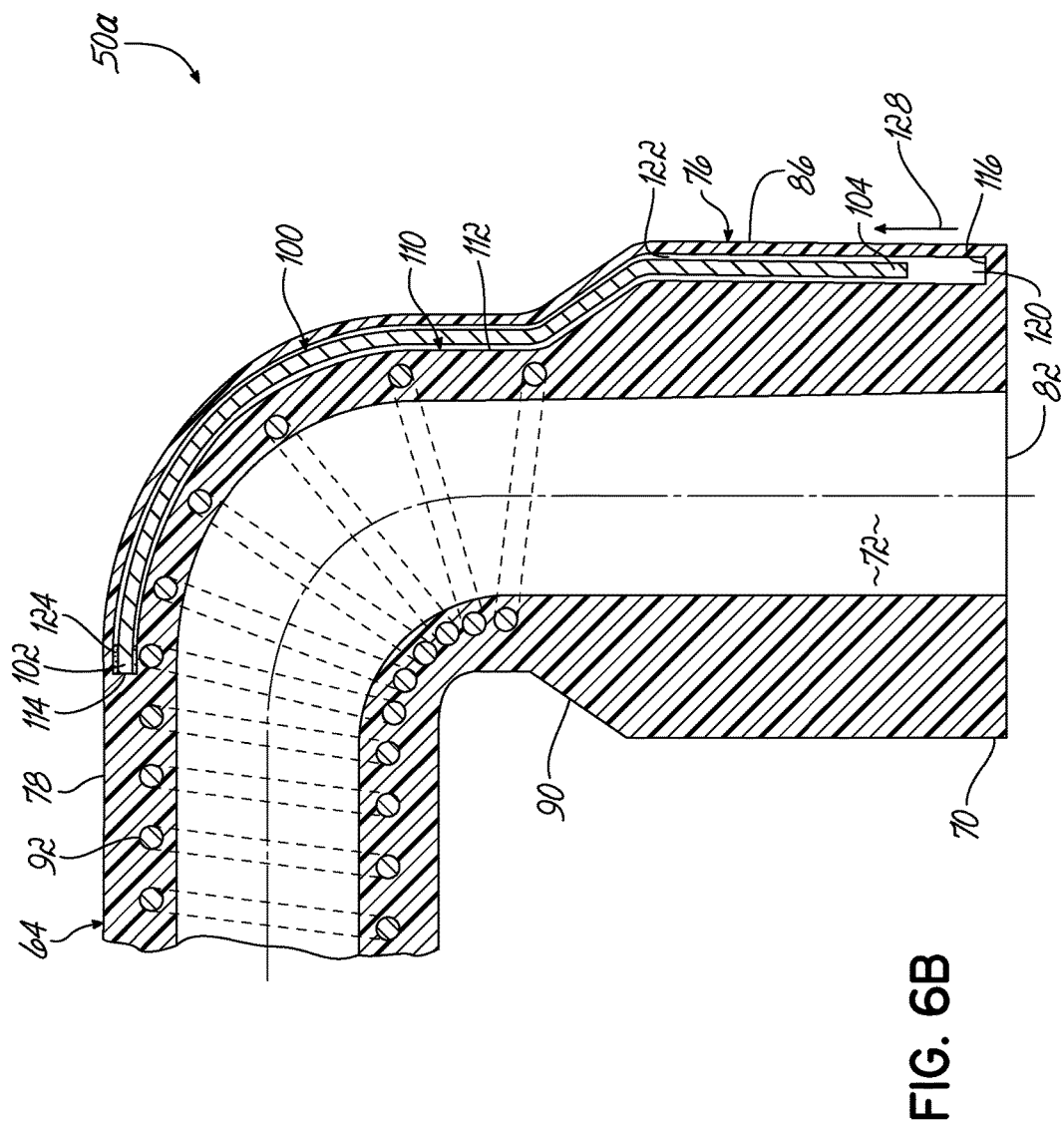
FIG. 6B is a cross-sectional view similar to FIG. 6, showing the malleable cannula in a second bent configuration.
Figure 7:
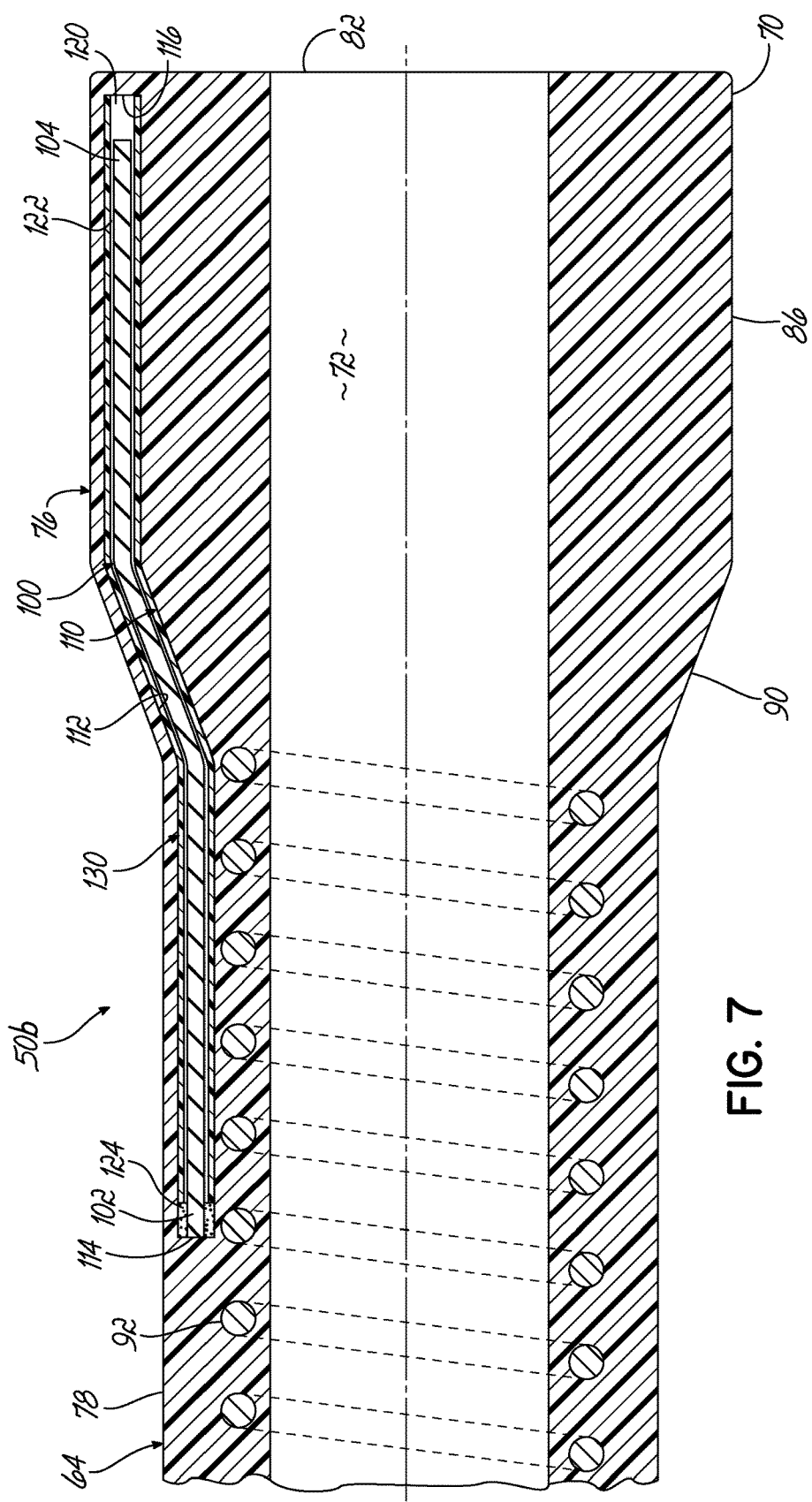
FIG. 7 is a cross-sectional view similar to FIG. 3, showing a distal portion of a malleable cannula of another embodiment in accordance with the principles of the invention.

Referring to FIGS. 6A and 6B, a distal portion of another exemplary embodiment of a malleable cannula 50a is shown. Similar reference numerals refer to similar features shown in FIGS. 2 and 3. In this embodiment, the proximal end 102 of the malleable member 100 is affixed to the first end 114 of the channel 110 with an affixing agent 124, for example with a urethane heat weld, a silicone RTV, or any other suitable adhesive bonding material. The malleable cannula 50a is shown in first and second bent configurations in which the cannula 50a has been bent into first and second formed shapes, for example to accommodate anatomical structure adjacent to the cannula 50b during use.

As shown in FIG. 6A, the malleable cannula 50a is shown in a first bent configuration in which the cannula 50a has been bent along its longitudinal axis at a longitudinal location of the medial portion 78 of the body wall 64 that includes the malleable member 100. In particular, the cannula 50b is shown bent along a plane defined jointly by the longitudinal axis of the body wall 64 and a longitudinal axis of the malleable member 100. In the first bent configuration shown, the distal hub 76 has been bent upwardly at an angle of approximately ninety degrees relative to the medial portion 78 of the body wall 64. Additionally, in the first bent configuration shown, the malleable member 100 is provided at an inner radius of the bent cannula body wall 64. Accordingly, when the cannula 50a is bent toward the first bent configuration, the malleable member 100 slides longitudinally relative to the channel wall 112 such that the unfixed distal end 104 of the malleable member 100 slides through the gap 120 toward the second end 116 of the channel 110, as indicated by arrow 126. Furthermore, though not shown, a radially outer portion of the cannula body wall 64 forming the channel wall 112 may flex slightly radially inward toward the longitudinal axis of the cannula 50a when the cannula 50a is bent toward the first bent configuration shown.

Referring to FIG. 6B, the malleable cannula 50a is shown in a second bent configuration substantially opposite of the first bent configuration shown in FIG. 6A. In particular, the malleable member 100 is provided at an outer radius of the bent cannula body wall 64. Accordingly, when the cannula 50a is bent toward the second bent configuration, the malleable member 100 slides longitudinally relative to the channel wall 112 such that the unfixed distal end 104 of the malleable member 100 withdraws away from the second end 116 of the channel 110, as indicated by arrow 128, thereby lengthening the gap 120.

While only first and second bent configurations are shown herein, persons skilled in the art will appreciate that a malleable cannula such as cannula 50 or 50a, may be bent along its longitudinal axis into any number of possible bent configurations to provide any desired formed shape of the cannula. For example, the distal hub 76 of cannula 50a may be formed into a bent configuration that is in between a neutral configuration shown in FIG. 3 and the first or second bent configurations shown in FIGS. 6A and 6B.

Furthermore, while the bent figurations shown in FIGS. 6A and 6B include bending the body wall 64 along a plane in which the malleable member 100 lies, persons skilled in the art will appreciate that the cannula 50a, or other Cannulae according to other embodiments, may be bent along a plane that does not include the malleable member 100. For example, though not shown, the cannula 50a may be bent along a plane that is transverse to the plane jointly defined by the longitudinal axis of the body wall 64 and the longitudinal axis of the malleable member 100.

Referring to FIG. 7, a distal portion of another exemplary embodiment of a malleable cannula 50b is shown. Similar reference numerals refer to similar features shown in FIGS. 2 and 3. In this embodiment, the channel wall 112 is lined with a low-friction channel liner 130 decreasing friction between the malleable member 100 and the channel wall 112 when the malleable member 100 slides longitudinally relative to the channel wall 112 when the cannula 50b is bent along its longitudinal axis into a formed shape. The channel liner 130 may extend continuously or discontinuously along any suitable length of the channel wall 112. For example as shown, the liner 130 may extend continuously for substantially the entire length of the channel wall 112. A longitudinally extending gap 122 may be provided between the liner 130 and the malleable member 100 when the cannula 50b is in a neutral, non-bent configuration, as shown. Alternatively, the cannula 50b may be formed such that the liner 130 directly contacts the malleable member 100 and no gap 122 is provided when the cannula 50b is in the neutral position. The channel liner 130 may be formed of any suitable material having a coefficient of friction that is lower than that of the material forming the channel wall 112. For example, in one embodiment the liner 130 may be formed of polytetrafluoroethylene (PTFE).

Still referring to FIG. 7, while the proximal end 102 of the malleable member 100 is shown affixed to the first end 114 of the channel 110 with an affixing agent 124, persons skilled in the art will appreciate that the proximal end 102 may be fixedly connected to the body wall 64 at the first end 114 of the channel 110 through any suitable fastening method. For example, as shown in FIG. 3, the proximal end 102 of the malleable member 100 may be embedded within the body wall 64 at the first end 114 of the channel 110. In that regard, malleable Cannulae as disclosed herein may be provided with a low-friction channel liner, such as liner 130.

While the present invention has been illustrated by the description of specific embodiments thereof, and while the embodiments have been described in considerable detail, it is not intended to restrict or in any way limit the scope of the appended claims to such detail. The various features discussed herein may be used alone or in any combination. Additional advantages and modifications will readily appear to those skilled in the art. The invention in its broader aspects is therefore not limited to the specific details, representative apparatus and methods and illustrative examples shown and described. Accordingly, departures may be made from such details without departing from the scope or spirit of the general inventive concept.

What is claimed is:

1. A malleable cannula for fluidically coupling with an anatomical structure, comprising:
   a flexible cannula body wall having a proximal end, a distal end, and a lumen extending longitudinally between the proximal end and the distal end, the proximal end defining a first opening to the lumen and the distal end defining a second opening to the lumen;
   a channel defined by a portion of the cannula body wall and extending longitudinally from the distal end toward the proximal end, the channel having a first end oriented toward the proximal end; and
   a malleable member provided within the channel and fixedly connected to the cannula body wall at the first end of the channel, the malleable member configured to assume and maintain a formed shape of the cannula body wall;
   wherein a proximal end of the malleable member is fixedly connected to the cannula body wall at the first end of the channel and a distal end of the malleable member extends freely toward the distal end of the cannula body wall; and
   wherein the channel includes a second end oriented toward the distal end of the cannula body wall, and the channel is sized to provide a longitudinal gap between the second end of the channel and the distal end of the malleable member such that the distal end of the malleable member slides through the longitudinal gap without contacting the second end of the channel when the cannula body wall is bent along its longitudinal axis at a longitudinal location that includes the malleable member.

2. The malleable cannula of claim 1, wherein the proximal end of the malleable member is embedded within the cannula body wall at the first end of the channel.

3. The malleable cannula of claim 1, wherein the proximal end of the malleable member is heat welded to the first end of the channel.

4. The malleable cannula of claim 1, wherein the proximal end of the malleable member is adhesively bonded to the first end of the channel.

5. The malleable cannula of claim 1, further comprising:
   a flexible reinforcement member embedded within the cannula body wall and extending longitudinally, the flexible reinforcement member configured to substantially maintain a cross-sectional shape of the lumen when the cannula body wall is bent along its longitudinal axis,
   wherein the channel is provided radially outward of the flexible reinforcement member.

6. The malleable cannula of claim 5, wherein the distal end of the malleable member extends distally beyond a distal end of the flexible reinforcement member.

7. The malleable cannula of claim 1, wherein the malleable member includes a malleable strip having a rounded cross-sectional shape.

8. The malleable cannula of claim 1, wherein the malleable cannula includes a malleable distal portion and a non-malleable proximal portion.

9. A medical fluid transfer system for coupling into fluidic communication with an interior portion of an anatomical structure, comprising:
   the malleable cannula of claim 1, wherein the distal end of the cannula body wall is fitted with a cannula tip configured to be inserted into the interior portion of the anatomical structure; and
   a fluid pump operatively coupled with the distal end of the cannula body wall.

10. A method of positioning a malleable cannula relative to an anatomical structure of a patient, the malleable cannula including a flexible cannula body wall having a proximal end, a distal end, and a lumen that extends longitudinally between the proximal end and the distal end, the proximal end defining a first opening to the lumen and the distal end defining a second opening to the lumen, the malleable cannula further including a cannula tip coupled to the distal end of the cannula body wall, the method comprising:
   inserting the cannula tip into an interior portion of the anatomical structure so that the lumen is in fluidic communication with the interior portion; and
   bending the cannula body wall along its longitudinal axis into a formed shape to accommodate an outer periphery of the anatomical structure or of an adjacent structure;
   wherein bending the cannula body wall into the formed shape includes bending a malleable member that substantially maintains the formed shape, the malleable member arranged within a channel extending longitudinally from the distal end of the cannula body wall toward the proximal end, the channel having a first end oriented toward the proximal end;
   wherein the channel is bounded in a radial direction by a channel wall, wherein a proximal end of the malleable member is fixedly connected to the cannula body wall at the first end of the channel and a distal end of the malleable member extends freely toward the distal end of the cannula body wall, and wherein bending the cannula body wall into the formed shape includes permitting the distal end of the malleable member to slide longitudinally relative to the channel wall; and wherein the channel includes a second end oriented toward the distal end of the cannula body wall, and the channel is sized to provide a longitudinal gap between the second end of the channel and the distal end of the malleable member, wherein bending the cannula body wall into the formed shape includes permitting the distal end of the malleable member to slide longitudinally through the longitudinal gap without contacting the second end of the channel.

11. The method of claim 10, wherein the proximal end of the malleable member is embedded within the cannula body wall at the first end of the channel.

* * * * *